US012697080B2

(12) United States Patent
Kruse et al.

(10) Patent No.: US 12,697,080 B2
(45) Date of Patent: Aug. 4, 2026

(54) SYSTEMS FOR A HEAT TRANSFER BOLTED JOINT

(71) Applicant: GE Precision Healthcare LLC, Waukesha, WI (US)

(72) Inventors: Kevin S Kruse, Muskego, WI (US); Richie Tran, Milwaukee, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 205 days.

(21) Appl. No.: 18/763,840

(22) Filed: Jul. 3, 2024

(65) Prior Publication Data
US 2026/0007379 A1    Jan. 8, 2026

(51) Int. Cl.
| | |
|---|---|
| *A61B 6/00* | (2024.01) |
| *A61B 6/03* | (2006.01) |
| *A61B 6/42* | (2024.01) |
| *F16B 5/02* | (2006.01) |

(52) U.S. Cl.
CPC ............ *A61B 6/4488* (2013.01); *A61B 6/032* (2013.01); *A61B 6/4266* (2013.01); *F16B 5/0241* (2013.01)

(58) Field of Classification Search
CPC ..... A61B 6/4488; A61B 6/032; A61B 6/4266; A61B 6/482; A61B 6/4233; A61B 6/4241; A61B 6/035
See application file for complete search history.

(56) References Cited

U.S. PATENT DOCUMENTS

| | | |
|---|---|---|
| 9,525,195 B2 | 12/2016 | Wyatt et al. |
| 2015/0071401 A1* | 3/2015 | Lacey ...................... G01T 1/16 378/19 |

FOREIGN PATENT DOCUMENTS

| | | | | |
|---|---|---|---|---|
| CN | 105338903 A | * | 2/2016 | ........... A61B 6/4233 |
| KR | 20140093350 A | | 7/2014 | |

OTHER PUBLICATIONS

"Application Note—Physical Constants of Pure Indium," Indium Website, Available Online at https://www.indium.com/products/metals/indium/#documents, Available as Early as Aug. 8, 2020, 2 pages.
EP application 25182286.2 filed Jun. 12, 2025—extended Search Report issued Nov. 11, 2025; 8 pages.

* cited by examiner

*Primary Examiner* — Casey Bryant
(74) *Attorney, Agent, or Firm* — McCoy Russell LLP

(57) ABSTRACT

Systems are provided a heat transfer bolted joint of an X-ray detector module. The heat transfer bolted joint includes a first surface comprising an alignment protrusion, a first alignment datum vertically extending from the alignment protrusion, a first bolt hole passing through the alignment protrusion, a compressible metal washer circumferentially surrounding the alignment protrusion and in direct face-sharing contact with the first surface, and a second surface including a second alignment datum adapted to mate to the first alignment datum, and a second bolt hole passing through the second surface. The second surface is in direct face-sharing contact with the compressible metal washer and with the alignment protrusion.

20 Claims, 10 Drawing Sheets

SYSTEMS FOR A HEAT TRANSFER BOLTED JOINT

TECHNICAL FIELD

Embodiments of the subject matter disclosed herein relate to systems for a bolted joint adapted to transfer heat.

BACKGROUND

A computed tomography imaging system may include a detector module including a rail assembly to which a plurality of X-ray detector units may be coupled. In some examples, the X-ray detector units may be photon counting computed tomography (PCCT) detector units. Components of the X-ray detector unit may output a large amount of heat. A heat management strategy may direct heat away from the X-ray detector units to the rail assembly.

BRIEF DESCRIPTION

In one embodiment, a heat transfer bolted joint of an X-ray detector module, comprising a first surface comprising an alignment protrusion, a first alignment datum vertically extending from the alignment protrusion, a first bolt hole passing through the alignment protrusion, a compressible metal washer circumferentially surrounding the alignment protrusion and in direct face-sharing contact with the first surface, wherein the compressible metal washer is compressible in a vertical direction and is positioned essentially within the heat transfer bolted joint, and a second surface including a second alignment datum mated to the first alignment datum, and a second bolt hole passing through the second surface, wherein the second surface is in direct face-sharing contact with the compressible metal washer and the alignment protrusion.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, herein below:

FIGS. 1 and 3-6 are shown approximately to scale, however, other dimensions may be used if desired.

DETAILED DESCRIPTION

Figure 3:
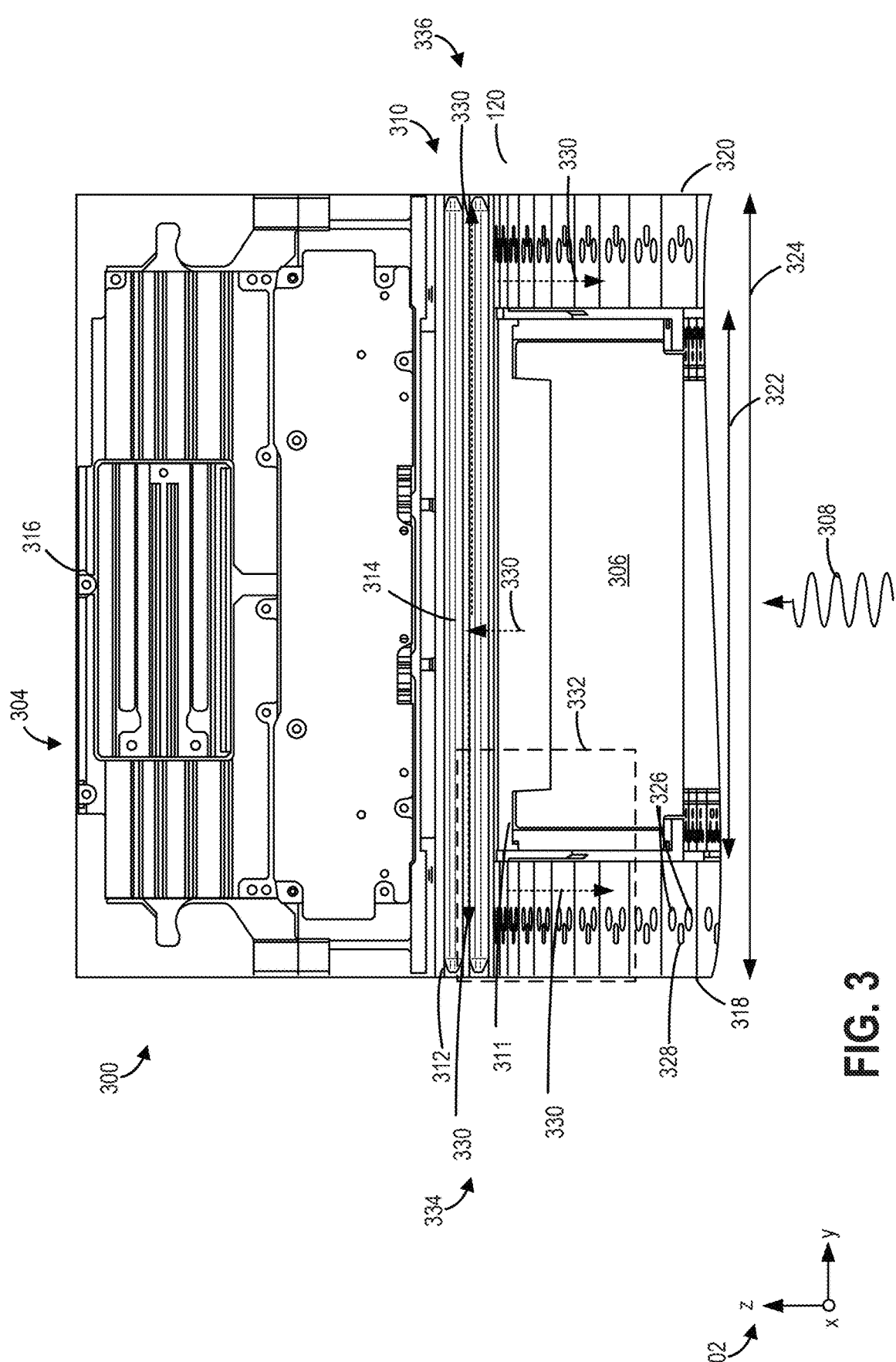
FIG. 3 shows a view of the detector module, in accordance with one or more embodiments of the present disclosure.
Figure 4:
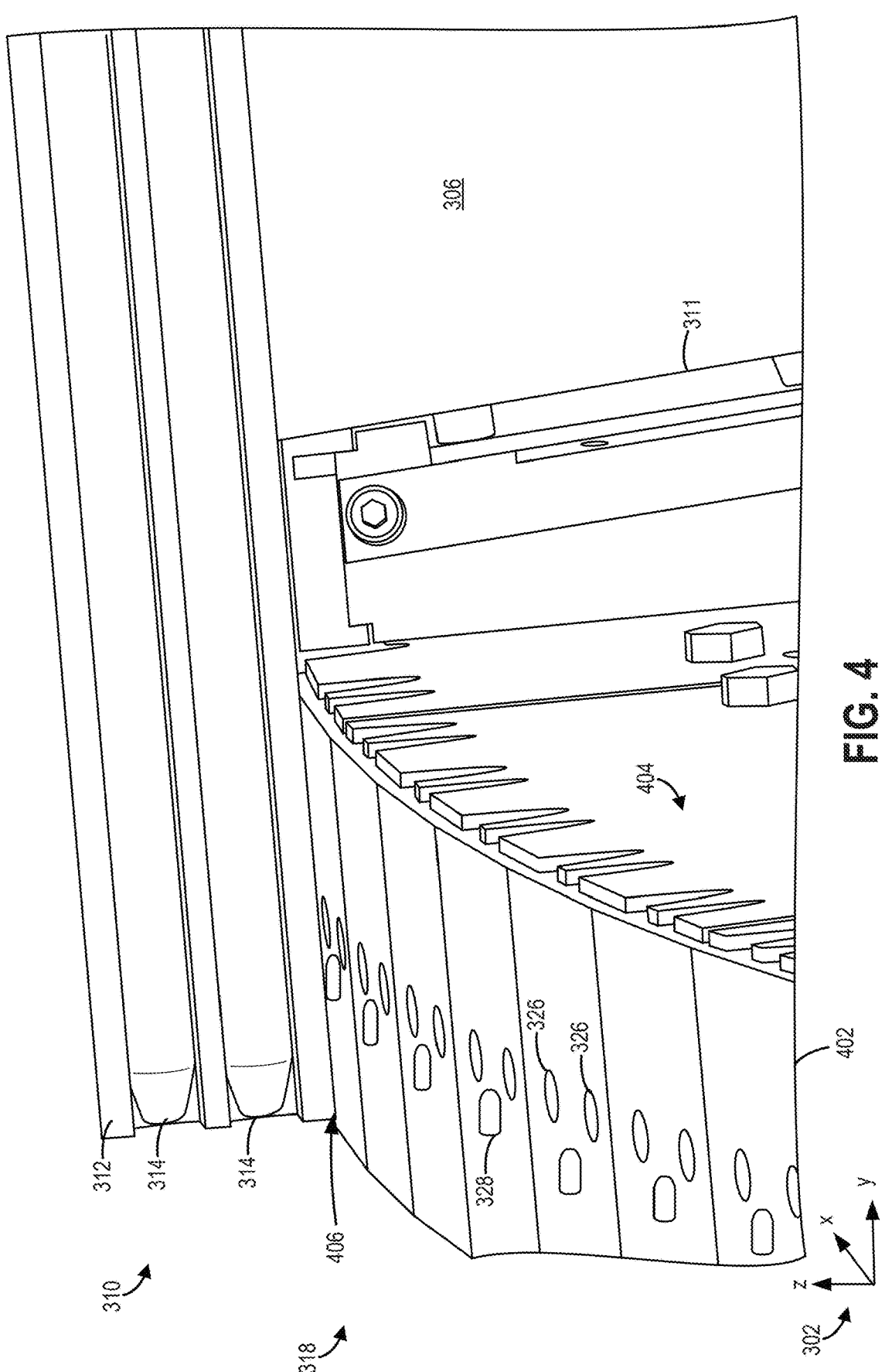
FIG. 4 shows a close view of the rail assembly and beam assembly, in accordance with one or more embodiments of the present disclosure.
Figure 5:
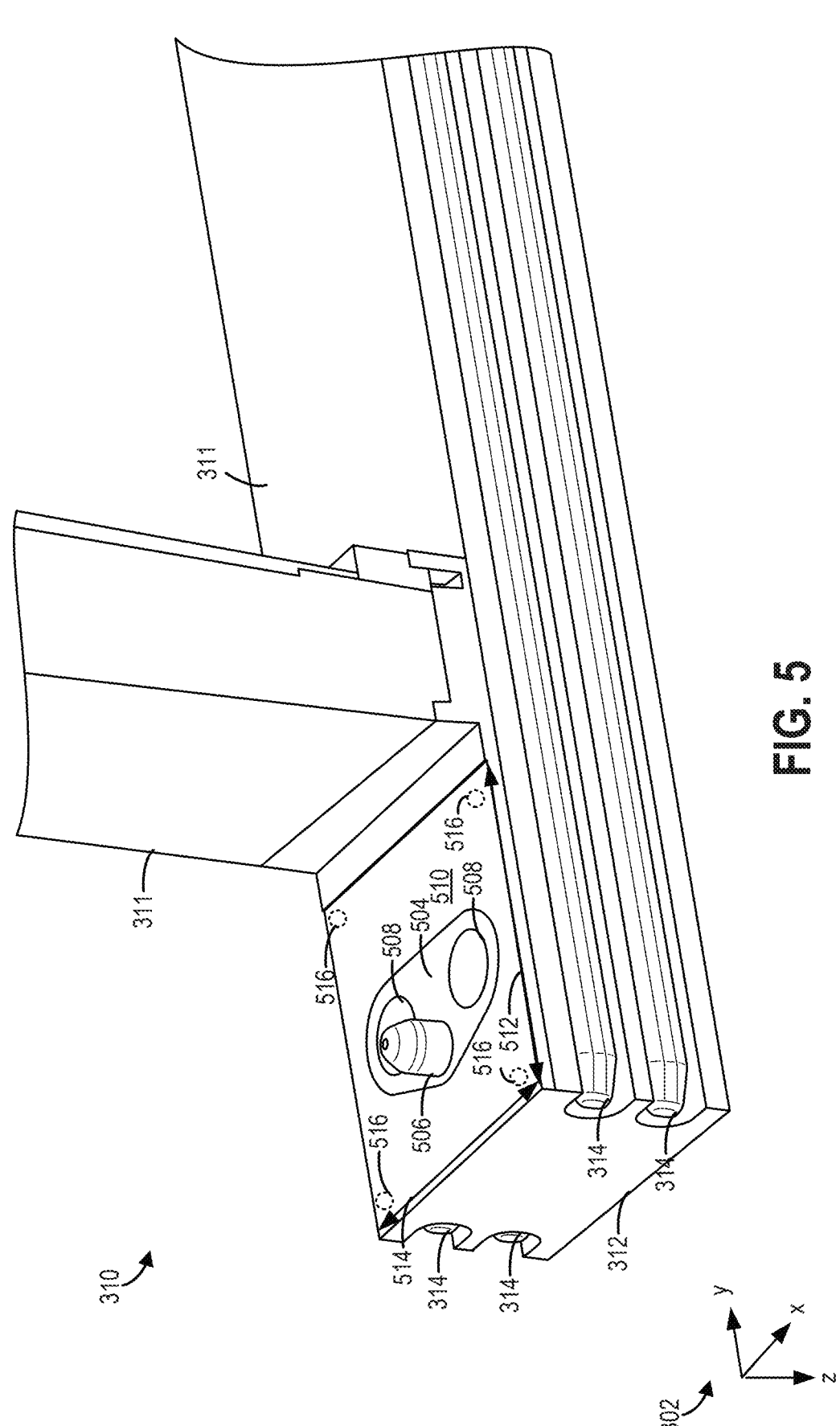
FIG. 5 shows a view of the beam assembly, in accordance with one or more embodiments of the present disclosure.
Figure 6:
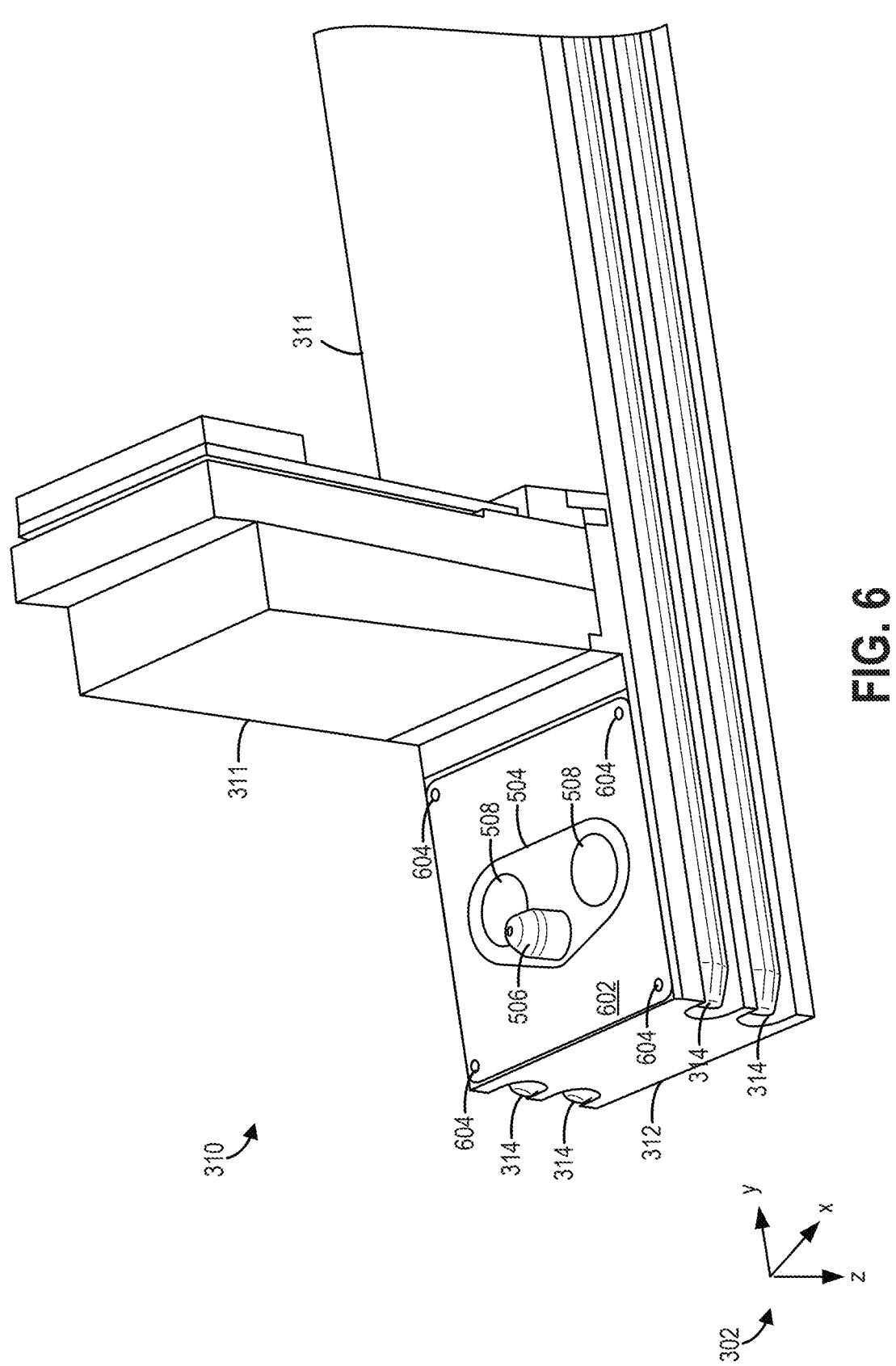
FIG. 6 shows a view of the beam assembly and washer, in accordance with one or more embodiments of the present disclosure.
Figure 9:
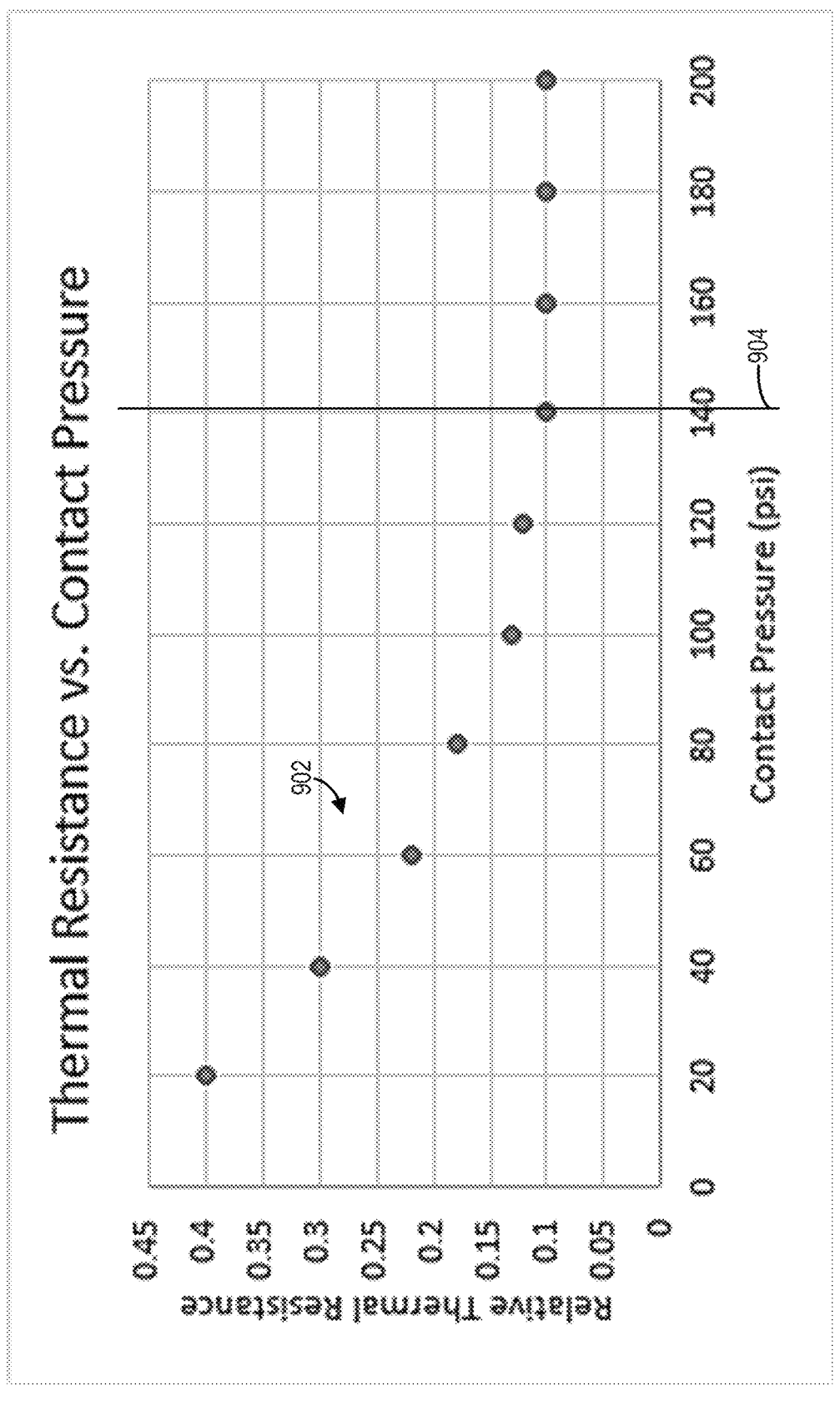
FIG. 9 shows a graph of thermal resistance as function of pressure in accordance with one or more embodiments of the present disclosure.
Figure 10:
FIG. 10 shows a model of contact pressure at the interface between the beam assembly and the rail assembly, in accordance with one or more embodiments of the present disclosure.

The following description relates to systems for a heat transfer bolted joint. The heat transfer bolted joint may further be adapted to have a high spatial tolerance. The heat transfer bolted joint may couple a beam assembly with a rail assembly in a detector module of a computed tomography (CT) imaging system, such as the CT imaging system shown in FIG. 1 and FIG. 2. An example of a detector module is shown in FIG. 3. The detector module may include a plurality of photon counting computed tomography (PCCT) detector units. For clarity, a single PCCT detector unit is shown in FIG. 3. The PCCT detector units may each include components such as power electronics which generate heat. To prevent performance degradation of the PCCT detector units, the detector module may include components configured to transfer heat away from the PCCT detector units. As one example, the PCCT detector units may include a beam assembly, the beam assembly including heat conduction channels positioned to draw heat away from the power electronics. The beam assembly may be supported at lateral ends by first and second rail assemblies and the heat may be further transferred from the ends of the beam assembly to the rail assemblies to be further dissipated by heat management features of the detector module. For this reason, a joint between the beam assembly and rail assembly may be a heat transfer bolted joint, adapted to reduce thermal resistance. Additionally, the plurality of PCCT detector units may be precisely positioned within the detector module with a small amount of tolerance. For this reason, the joint between the beam assembly and the rail assembly may also be adapted for a high spatial tolerance and precise positioning of the beam assembly with respect to the rail assembly. A close view of the joint between the beam assembly and rail assembly including the PCCT detector units is shown in FIG. 4. A view of the beam module portion of the joint is shown in FIG. 5. The joint may include an alignment protrusion as shown in FIG. 5. A compressible metal washer may be positioned around the alignment protrusion as shown in FIG. 6. The compressible metal washer may be adapted to be compressed when the beam module is joined to the rail module by bolts. Compression of the compressible metal washer may decrease thermal resistance between the beam module and rail module and allow for bolting the joint to a precise and reproducible height. The heat transfer thermal joint is shown in a cross-sectional view in FIG. 7 and a method for assembling the heat transfer bolted joint is shown as a flowchart in FIG. 8. A graph of thermal resistance as a function of pressure applied to the compressible metal washer in the joint is shown in FIG. 9. Finite element modeling of pressure within the joint is shown in FIG. 10.

Figure 1:
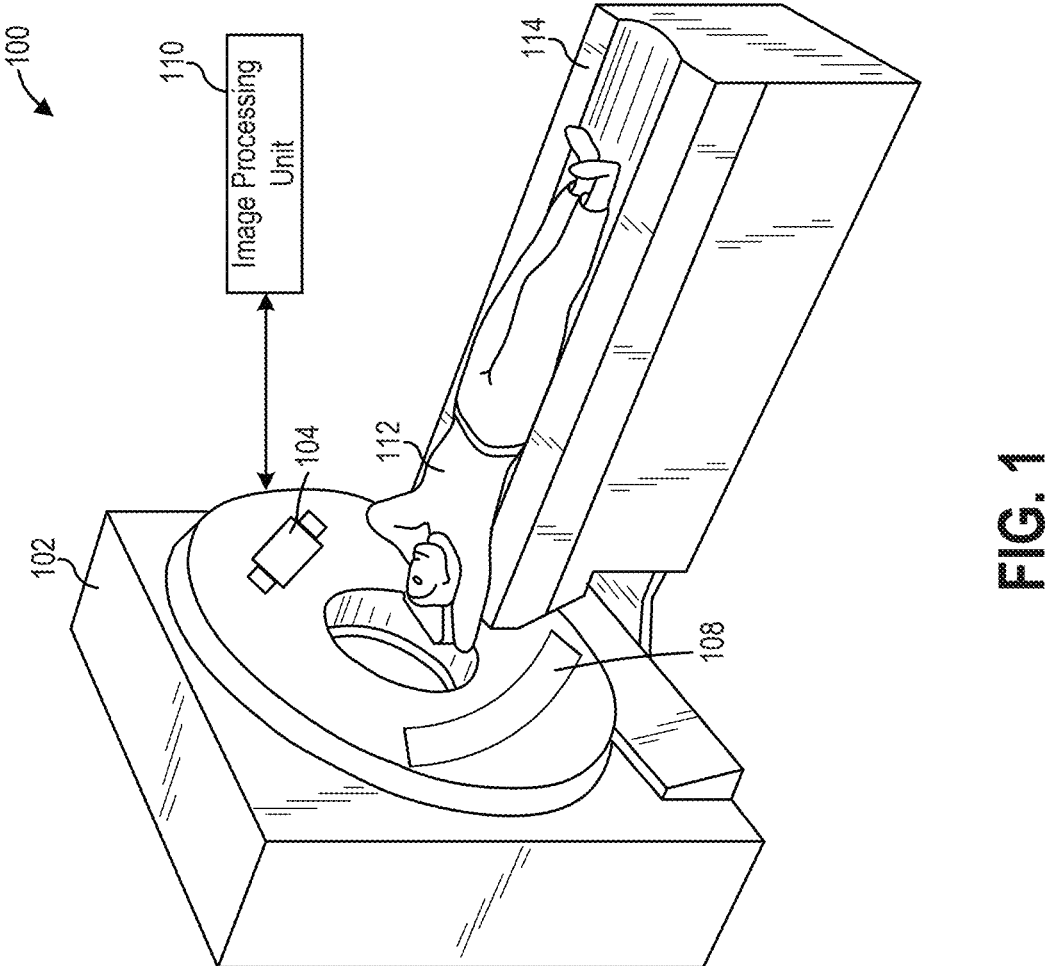
FIG. 1 shows a pictorial view of a CT imaging system, in accordance with one or more embodiments of the present disclosure.

Turning now to FIG. 1, it illustrates an exemplary computed tomography system (e.g., CT system) 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one X-ray source 104 configured to project a beam of X-ray radiation 106 (see FIG. 2) for use in imaging the subject 112 laying on a table 114. Specifically, the X-ray source 104 is configured to project the X-ray radiation beams 106 towards a detector array 108 positioned on the opposite side of the gantry 102. Although FIG. 1 depicts a single X-ray source 104, in certain embodiments, multiple X-ray sources and detectors may be employed to project a plurality of X-ray radiation beams for acquiring projection data at different energy levels corresponding to the patient. In some embodiments, the X-ray source 104 may enable dual-energy gemstone spectral imaging (GSI) by rapid peak kilovoltage (kVp) switching. In some embodiments, the X-ray detector employed is a photon-counting detector which is capable of differentiating X-ray photons of different energies. In other embodiments, two sets of X-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 including one or more processors configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use an analytic image reconstruction approach such as FBP in addition to an iterative image reconstruction approach.

In some CT imaging system configurations, an X-ray source projects a cone-shaped X-ray radiation beam which is collimated to lie within an X-Y-Z plane of a Cartesian coordinate system and generally referred to as an "imaging plane." The X-ray radiation beam passes through an object being imaged, such as the patient or subject. The X-ray radiation beam, after being attenuated by the object, impinges upon an array of detector elements. The intensity of the attenuated X-ray radiation beam received at the detector array is dependent upon the attenuation of an X-ray radiation beam by the object. Each detector element of the array produces a separate electrical signal that is a measurement of the X-ray beam attenuation at the detector location. The attenuation measurements from all the detector elements are acquired separately to produce a transmission profile.

In some CT systems, the X-ray source and the detector array are rotated with a gantry within the imaging plane and around the object to be imaged such that an angle at which the X-ray beam intersects the object constantly changes. A group of X-ray radiation attenuation measurements, e.g., projection data, from the detector array at one gantry angle is referred to as a "view." A "scan" of the object includes a set of views made at different gantry angles, or view angles, during one revolution of the X-ray source and detector.

The X-ray source 104 includes an anode and a cathode. Electrons emitted by the cathode (e.g., resulting from energization of the cathode) may be intercepted by a target arranged at or near the anode. Electrons intercepted by the target may release energy in the form of X-rays, with the X-rays being directed toward the detector array 108. An area of the target surface that receives the electrons from the cathode and forms the emitted X-rays may be referred to herein as a "focal spot." The emitted X-rays may be focused on a portion of the scanned subject 204, at an "effective focal spot". A size of the effective focal spot may depend on an angle of the actual focal spot (e.g., on the target surface). For example, a small effective focal spot may be desirable when scanning a small area, while a large effective focal spot may be desirable when scanning a larger area.

In some embodiments, an X-ray generation system including the X-ray source 104 may move and/or shape the focal spot. For example, the X-ray generation system may increase or decrease a size of the focal spot. Additionally, in some embodiments, the X-ray generation system may generate a composite focal spot, where the composite focal spot is a combination of two or more discrete focal spots. For example, two discrete focal spots located apart from each other may be combined to produce a single, composite focal spot.

Figure 2:
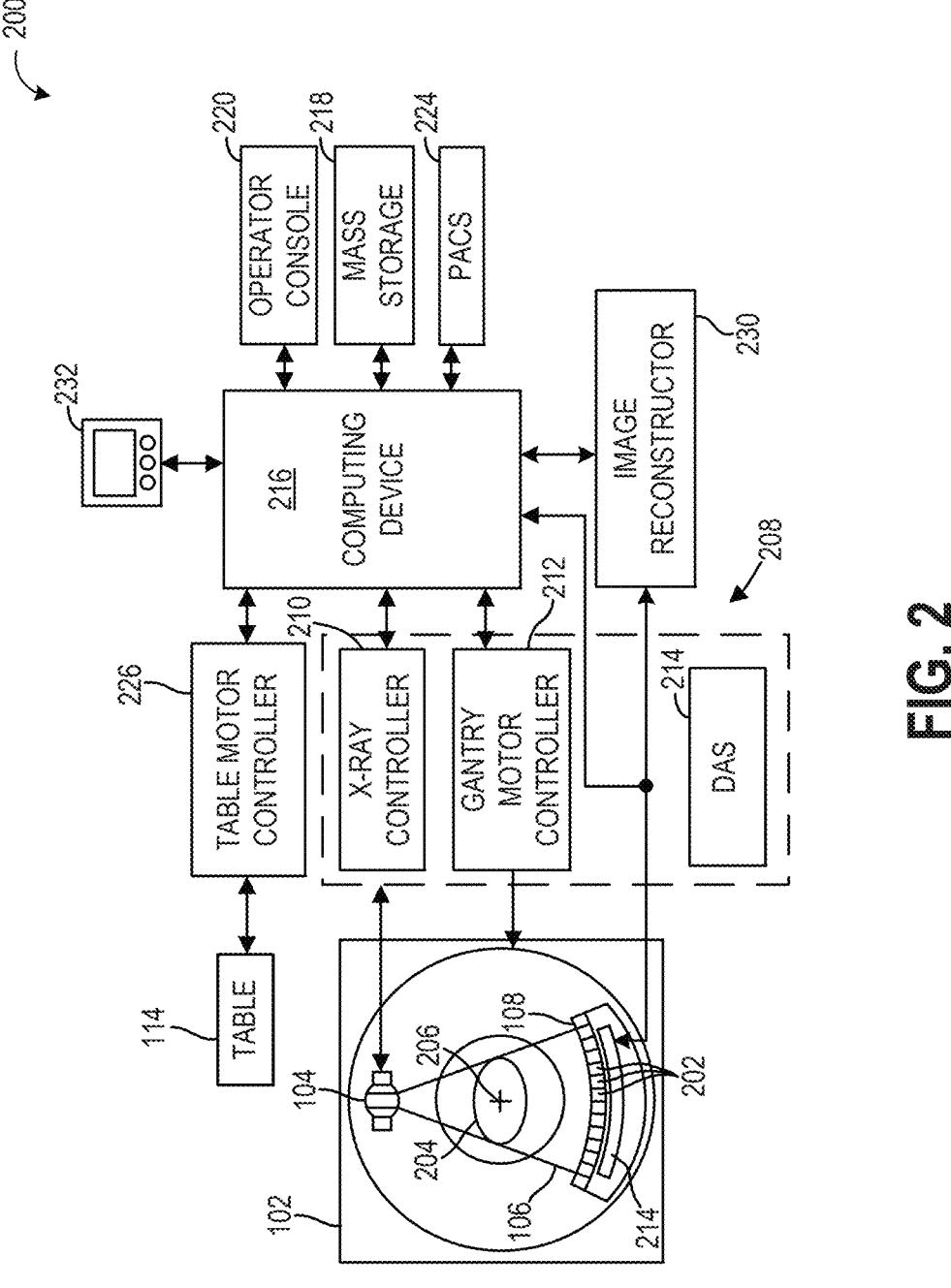
FIG. 2 shows a block schematic diagram of an exemplary CT imaging system, in accordance with one or more embodiments of the present disclosure.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector units 202 (e.g., detector modules) that together sense the X-ray radiation beam 106 (see FIG. 1) that pass through the subject 204 (such as a patient) to acquire corresponding projection data. In some embodiments, the detector array 108 may be fabricated in a multi-slice configuration including the plurality of detector units 202, where one or more additional rows of the detector units 202 are arranged in a parallel configuration for acquiring the projection data. In an exemplary embodiment, the detector array 108 may include one or more detector module, such as the detector module described below in FIGS. 3-5. The detector module may be configured to transfer heat away from detector units 202 as described further below.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the X-ray source 104 and the detector array 108 rotate, the detector array 108 collects data of the attenuated X-ray beams. The data collected by the detector array 108 undergoes pre-processing and calibration to condition the data to represent the line integrals of the attenuation coefficients of the scanned subject 204. The processed data are commonly called projections. In some examples, the individual detectors or detector units 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a 3D volumetric image of the basis material, for example, bone, soft tissue, and/or contrast agent, in the imaged volume.

Once reconstructed, the basis material image produced by the imaging system 200 reveals internal features of the subject 204, expressed in the densities of two or more basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the X-ray source 104. In certain embodiments, the control mechanism 208 further includes an X-ray controller 210 configured to provide power and timing signals to the X-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector units 202 and convert the analog data to digital signals for subsequent processing. The data sampled and digitized by the DAS 214 is transmitted to a computer or computing device 216 including one or more processors. In one example, the computing device 216 stores the data in a storage device or mass storage 218. The storage device 218, for example, may be any type of non-transitory memory and may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the X-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector units 202. Subsequently, an image reconstructor 230 uses the sampled and digitized X-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

Turning now to FIG. 3, a view of a portion of an X-ray detector module 300, herein referred to as detector module 300, is shown. Detector module 300 may be included in a detector array, such as detector array 108 of FIG. 1 and/or may be one of the plurality of detector units 202 shown in FIG. 2. A reference axis 302 is provided for comparison between the view of FIGS. 3-7. Reference axis 302 includes an x-axis, y-axis, and z-axis. The x-axis may be parallel to a longitudinal axis with respect to detector module 300 and the y-axis may be parallel to a lateral axis with respect to detector module 300. The z-axis may correspond to a vertical axis.

Detector module 300 may include a PCCT detector unit 304. Detector module 300 may include a plurality of PCCT detector units stacked along the longitudinal direction within detector module 300, and each positioned parallel to PCCT detector unit 304 along the x-axis. PCCT detector unit 304 may include a sensor assembly 306. Sensor assembly 306 may include a plurality of photon counting sensors positioned to interact with incoming x-rays 308 and adapted to convert incoming x-rays 308 into electrical signals.

PCCT detector unit 304 may further include a beam assembly 310. Sensor assembly 306 may be directly physically coupled to beam assembly 310. Beam assembly 310 may include a bracket portion 311 and a heat transfer portion 312. Bracket portion 311 may extend vertically (e.g., along the z-axis) from a first side of heat transfer portion 312. Bracket portion 311 may be in direct face-sharing contact with at least three sides of sensor assembly 306. Bracket portion 311 may be adapted to securely position the sensor assembly 306 within detector module 300.

Heat transfer portion 312 may be shaped as a rectangular prism and may extend laterally past edges of bracket portion 311. A lateral length of heat transfer portion 312 may be longer than a lateral length of bracket portion 311. Heat transfer portion 312 may include heat pipes 314. Heat pipes 314 may extend laterally along each longitudinal face of heat transfer portion 312. As one example, heat transfer portion 312 may include two heat pipes 314, although greater or fewer number of heat pipes 314 are also considered within the scope of the disclosure. Further, each longitudinal face of heat transfer portion may include indents in which heat pipes 314 sit. In this way, heat pipes 314 may not radially extend past the longitudinal face of heat transfer portion 312. A longitudinal length of heat transfer portion 31 and bracket portion 311 may be equivalent. PCCT detector unit 304 may further include a heat sink enclosure 316. Heat sink enclosure 316 may extend vertically from a second side of heat transfer portion 312. Heat sink enclosure 316 may be formed of aluminum and may encase a module board comprising power electronics configured to process and transfer data received from PCCT detector unit 304. The second side of heat transfer portion 312 may be opposite the first side across the z-axis.

Detector module 300 may further include a first rail assembly 318 and a second rail assembly 320. First rail assembly 318 and second rail assembly 320 may be positioned parallel to each other along longitudinal sides of detector module 300. First rail assembly 318 and second rail assembly 320 may be parallel to each other and the inner sides may be spaced apart by a distance 322. Herein, inner or interior may refer to between first rail assembly 318 and second rail assembly 320 along the y-axis while outer or exterior refers to the opposite faces long the y-axis (e.g., not between first rail assembly 318 and second rail assembly 320). Distance 322 may be substantially (within 5%) equivalent to a lateral length of bracket portion 311. PCCT detector unit 304 may be positioned transversely to first rail assembly 318 and second rail assembly 320 such that bracket portion 311 fits between the inner sides of first rail assembly 318 and second rail assembly 320 and a first end 334 and a second end 336 of heat transfer portion 312 rest on a vertical surface of the first and second rail assemblies. A distance 324 between outer sides of first rail assembly 318 and second rail assembly 320 may be substantially equivalent a lateral length of heat transfer portion 312.

The first end 334 and the second end 336 of heat transfer portion 312 each include portion of the first side of heat transfer portion 312 extending laterally past bracket portion 311. The aforementioned portions may be in face-sharing contact with a vertical side of first rail assembly 318 and second rail assembly 320. In this way, beam assembly 310 is coupled at either lateral end (e.g., first end 334 and second end 336) to the first rail assembly 318 and second rail assembly 320, respectively. The first vertical side of first rail assembly 318 and second rail assembly 320 may each include a plurality of bolt hole pairs 326. The plurality of bolt hole pairs 326 may be arranged in a longitudinal line along the first vertical sides of first rail assembly 318 and second rail assembly 320. Each bolt hole pair 326 may correspond to bolt holes of a beam assembly; such as beam assembly 310. The number of bolt hole pairs along first rail assembly 318 may be equivalent to a number of PCCT units 304 positioned in detector module 300.

A rail alignment datum 328 may be positioned longitudinally between the bolt holes of each of the plurality of bolt hole pairs 326. Herein, an alignment datum refers to feature configured to restrict movement of a part when the alignment datum is mated (e.g., in face-sharing contact) with a corresponding alignment datum. Further, rail alignment datum 328 may be positioned laterally closer to the outer edge of the rail assemblies than bolt hole pair 326. As one example rail alignment datum 328 may be an indent adapted to receive a corresponding protruding beam alignment datum. In an alternate example, rail alignment datum 328 may be a protrusion adapted to mate with a corresponding recessed beam alignment datum. In one example, when rail alignment datum 328 is mated with the beam alignment datum, the bolt hole pair 326 may be radially and axially aligned with corresponding bolt hole pairs formed in heat transfer portion 312. Further, the longitudinal and lateral position of beam assembly 310 relative to first rail assembly 318 and second rail assembly 320 may be controlled by the mating of the rail alignment datum with the beam alignment datum. The aligned bolt hole pairs may receive bolts adapted to affix PCCT detector unit 304 to first rail assembly 318 and second rail assembly 320. In this way, PCCT detector unit 304 may be secured within detector module 300 and prevented from relative movement while detector module 300 rotates around a patient during an imaging procedure as described above.

An interface between beam assembly 310 and first rail assembly 318 and an interface between beam assembly 310 and second rail assembly 320 may comprise a first heat transfer bolted joint and a second heat transfer bolted joint, respectively. As one example, the first heat transfer bolted joint and second heat transfer bolted joint may be identical in structure, but positioned at opposite lateral sides of beam assembly 310. As described above, the sensor assembly 306 may include power electronics which generate heat. Flow of heat is shown by arrows 330. Features such as heat pipes 314 may draw heat out of sensor assembly 306 and towards first rail assembly 318 and second rail assembly 320. Heat may be further transferred through the heat transfer bolted joint to each of first rail assembly 318 and second rail assembly 320. Each of first rail assembly 318 and second rail assembly 320 may include features not shown in FIG. 3 configured to further transfer heat away from detector module 300.

Additionally, the heat transfer bolted joint may be configured to precisely position beam assembly 310 with respect to first rail assembly 318 and second rail assembly 320. Precise positioning in the lateral and longitudinal directions may be demanded, at least partially due to a minimal clearance between adjacent PCCT detector units placed in detector module 300. For example, a clearance between adjacent PCCT detector units may be in a range of 0.025 mm to 0.035 mm. Further precise and accurate vertical positioning of beam assembly 310 may be demanded at least partially due to maintaining a calibrated distance between sensor assembly 306 and the X-ray emitter positioned opposite from detector module 300, as described above. An angular and vertical position of beam assembly 310 may be determined by a combination of the mated alignment datum (the angular position) and interface of an alignment protrusion combined with compressible metal washer (the vertical position) as described further below. Herein, each PCCT detector unit of the PCC plurality of PCCT detector unit may be positioned similarly to PCCT detector unit 306. For example, each beam assembly may couple similarly to the first and second rail assemblies and each interface may between each beam assembly and first and second rail assemblies may be heat transfer bolted joints.

Turning now to FIG. 4 a close view of the area outlined by box 332 in FIG. 3 is shown. A first vertical side 402 of first rail assembly 318 corresponding with the vertical side of first rail assembly 318 described above with respect to FIG. 3 is shown. Additionally, FIG. 4 shows an inner side 404 of first rail assembly 318 corresponding to the inner side of first rail assembly 318 described above with respect to FIG. 3. FIG. 4 also shows inner side 404 of first rail assembly 318 in face-sharing contact with bracket portion 311 of beam assembly 310. A heat transfer bolted joint 406 may be positioned at an interface between first rail assembly 318 and beam assembly 310. The interface is discussed further below with respect to the cross-section view shown in FIG. 7. It is understood that an interface between second rail assembly 320 and beam assembly 310 is substantially the same as shown in FIG. 4 but mirrored across a plane parallel to the x-z plane positioned at the midpoint of distance 324.

Turning now to FIG. 5, beam assembly 310 is shown. Assembly 316 and sensor assembly 306 are not shown for clarity. A first end of beam assembly 310 is shown in FIGS. 5-6 and it is understood that substantially the same features are also present at the second end of beam assembly 310.

The first end of beam assembly 310 includes a first surface 510 of heat transfer bolted joint. First surface 510 may comprise a rectangular portion of the first side of heat transfer portion 312 extending laterally past bracket portion 311 towards an outer edge of first rail assembly 318. A lateral length 512 of first surface 510 may be equivalent to the lateral length of first rail assembly 318 that extends past bracket portion 311. A longitudinal length 514 of first surface 510 may be equivalent to the longitudinal length of beam assembly 310. In some examples, first surface 510 may include divots 516. Divots 516 may be positioned at each of the four corners of first surface 510. Divots 516 may be formed by peening or otherwise impacting first surface 510 to form a concave, roughly circular divots 516.

First surface 510 may include an alignment protrusion 504. Alignment protrusion 504 may protrude a small vertical distance from first surface 510. As one example, the small vertical distance may be about (e.g., +/−5%) 0.2 mm. Alignment protrusion 504 may be spaced away from edges of beam assembly 310. Additionally, alignment protrusion 504 may be formed of the same material as first surface 510.

Beam alignment datum 506 and pair of bolt holes 508 may be positioned on alignment protrusion 504. Beam alignment datum 506 may be adapted to mate with rail alignment datum 328 to ensure correct lateral and longitudinal placement of beam assembly 310 within detector module 300. As described above, beam alignment datum 506 may include a protrusion, protruding vertically from alignment protrusion 504, and may mate with rail alignment datum 328, which is formed as a recess adapted to receive beam alignment datum 506. When beam alignment datum 506 is mated with rail alignment datum 328 bolt holes 508 are radially and axially aligned with bolt hole pair 326 of the rail assembly. Bolts may be adapted to mate with both bolt holes 508 of beam assembly 310 and bolt hole pair 326 of the rail assemblies. In this way, beam assembly 310 may be affixed to first rail assembly 318 and second rail assembly 320.

As one example, beam alignment datum 506 may be positioned longitudinally between bolt holes 508. Further, beam alignment datum 506 may be laterally unaligned with bolt holes 508. For example, beam alignment datum 506 may be laterally closer to first end 334 than bolt holes 508. Other configurations of beam alignment datum 506 and bolt holes 508 on alignment protrusion 504 are also considered.

Depending on a positioning of beam alignment datum 506 and bolt holes 508, a shape of alignment protrusion 504 may be adjusted such that bolt holes 508 pass through alignment protrusion 504 and beam alignment datum 506 protrudes from alignment protrusion 504. In some examples, alignment protrusion 504 may include more than one alignment protrusion 504, each of the alignment protrusions circumferentially surrounding beam alignment datum 506 and/or one or both of bolt holes 508. In some examples, may be a rounded shape, having no severe corners in the x-y plane. In some examples, alignment protrusion may be symmetrical about the lateral axis. In an alternate example, alignment protrusion 504 may be positioned on the vertical surface of first rail assembly 318 to circumferentially surround rail alignment datum 328 and bolt hole pair 326, and beam alignment datum 506 and beam holes 508 may be flush with first surface 510.

Turning now to FIG. 6, beam assembly 310 is shown with a compressible metal washer 602 in face-sharing contact with first surface 510. Compressible metal washer 602 may include a cutout shaped as alignment protrusion 504. In examples where the heat transfer bolted joint includes multiple alignment protrusions, the heat transfer bolted joint may also include more than one compressible metal washer. In further examples, one compressible metal washer 602 may be shaped with multiple cutouts to circumferentially surround each alignment protrusion. In this way, compressible metal washer 602 circumferentially surrounds alignment protrusion 504. Before the heat transfer bolted joint is assembled, compressible metal washer 602 may be a first vertical height (e.g., measured along the z-axis). The first vertical height may be larger than the vertical height of alignment protrusion 504. For example, compressible metal washer 602 may be 60-100 μm higher in the z-direction than alignment protrusion 504. In further examples, compressible metal washer 602 may be 70-80 μm higher in the z-direction than alignment protrusion 504.

In some examples, peening points 604 may be formed around an outer circumference of compressible metal washer 602. As one example, peening points 604 may be positioned at corners of compressible metal washer 602, but other placements and amounts of peening points 604 are also considered within the scope. The position of peening points 604 may be aligned in the x-y plane with positions of divots 516 of first surface 510. Peening points may be concave portions of compressible metal washer 602 which are pressed into divots 516. In this way, peening points 604 may hold compressible metal washer 602 in place relative to the first surface 510 during assembly of the heat transfer bolted joint. For example, beam assembly 310 may be inverted during assembly of detector module 300 such that compressible metal washer 602 would fall off of beam assembly 310 due to gravity if not for peening points 604.

Compressible metal washer 602 may be formed from a compressible metal having a high heat transfer coefficient (e.g., high thermal conductivity). As one example, a thermal conductivity of the compressible metal may be at least 80 W/mK. As a further example, the compressive strength of the compressible metal may be at most 2.14 MPa. As a further example, the hardness of the compressible metal may be at most 0.9HB. Further, the compressible metal washer 602 may remain solid under the operating temperature of the heat transfer bolted joint. For example, a melting point of the compressible metal washer may be greater than 50° C. Further, the compressible metal washer may be compressible, but may be stiff enough to remain in the heat transfer bolted joint when compressed and not be extruded from the heat transfer bolted joint. For example, when assembled, the compressible metal washer 602 is positioned essentially within the heat transfer bolted joint. For example, at least 95% of the volume of compressible metal washer 602 is between beam assembly 310 and the rail assembly, and not extruded outside of the interface. As one example, compressible metal washer 602 may be formed of indium or an alloy of indium.

Table 1 below compares performance of different compressible metal washers with respect to a temperature difference between the beam module and rail assembly measured on either side of the heat transfer bolted joint (e.g., heat transfer bolted joint 406).

TABLE 1

| Heat transfer performance of washers compared to a baseline | | | | |
|---|---|---|---|---|
| Washer Material | Baseline | Indium 1 | Indium 2 | Copper |
| Thermal Conductivity (W/mK) | n/a | 86 | 86 | 390 |
| Detector Temp (° C.) | 48.14 | 46.06 | 46.25 | 47.66 |
| Module to Rail delta C. ° | 2.94 | 1.00 | 1.03 | 2.33 |
| Washer vs baseline delta C. ° | n/a | 1.94 | 1.91 | 0.61 |

Table 1 compares performance of different compressible metal washers to a baseline. The baseline is assembling the joint without a compressible metal washer. A first (indium 1) and second (indium 2) washer are tested. The second indium washer is thicker (e.g., a greater height in the vertical direction) than the first indium washer. The results shown in table 1 indicate that presence of a washer increases the heat transfer when compared to a baseline. Additionally, both compressibility and thermal conductivity affect heat transfer performance of the washer in the heat transfer bolted joint and compressibility may be weighted higher than thermal conductivity for determining performance. As shown in Table 1, even though copper has a higher thermal conductivity than indium, it is less compressible and does not perform as well as the indium washer in the test.

Figure 7:
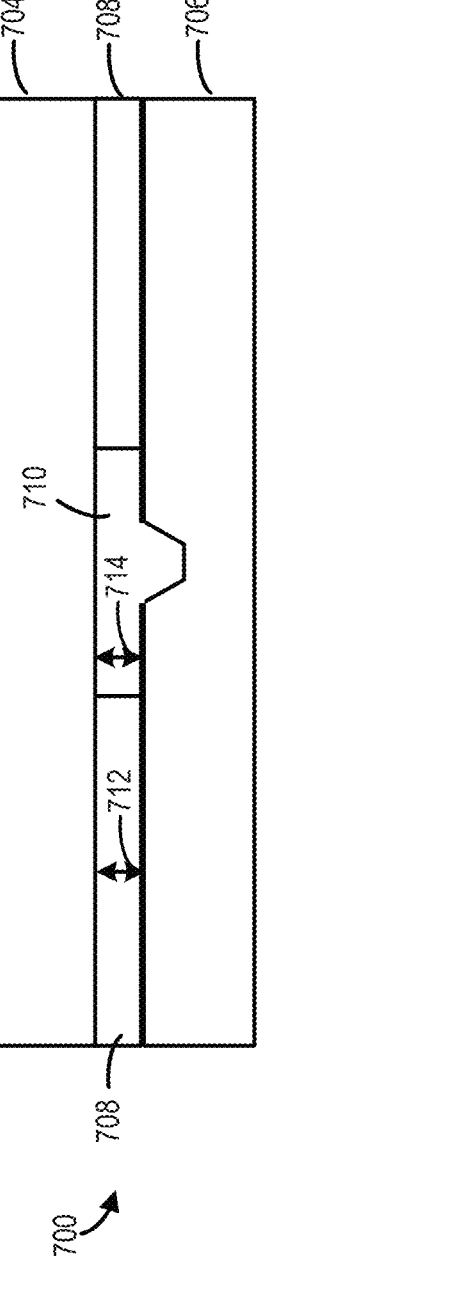
FIG. 7 shows a cross section view of the heat transfer bolted joint, in accordance with one or more embodiments of the present disclosure.
Figure 7:
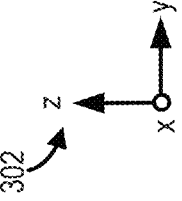

The heat transfer bolted joint may be formed when beam assembly 310 is joined to first rail assembly 318 and second rail assembly 320. A cross sectional view of a heat transfer bolted joint 700 is shown in FIG. 7. The cross section may be along the x or y axis, intersecting an alignment datum (such as beam alignment datum 506, but not the bolt holes). Heat transfer bolted joint 700 may correspond to heat transfer bolted joint 406, and may include a first surface 704, a second surface 706, and a compressible metal washer 708. In an exemplary embodiment, first surface 704 may be a surface of an end of a beam assembly such as first surface 510 of beam assembly 310, and a second surface 706 may a surface of a rail assembly, such as first rail assembly 318 and second rail assembly 320.

Alignment protrusion 710 may extend vertically from first surface 704. Alignment protrusion 710 may be in face-sharing contact with second surface 706. Further an alignment datum of first surface 704 is mated with and in face-sharing contact with a datum feature of second surface 706. Compressible metal washer 708 may be in face-sharing contact with both first surface 704 and second surface 706. A vertical height 712 of compressible metal washer 708 may be equivalent to a vertical height 714 of alignment protrusion 710. A material of first surface 704, alignment protrusion 710 and second surface 706 may be less compressible than compressible metal washer 708. In this way, when heat transfer bolted joint 700 is assembled compressible metal washer 708 may be compressed from a first, larger vertical height to be equivalent to vertical height 714 when alignment protrusion 710 is placed in face-sharing contact with the corresponding position on second surface 706. Further, a calibrated vertical position of the first surface with respect to the second surface may be reproducibly set by vertical height 714 of the alignment protrusion and may not be subject to how much compression is applied to compressible metal washer 708 during assembly. For this reason, the alignment protrusion may be essentially incompressible. In this way, the vertical height of the heat transfer bolted joint is calibrated to a demanded vertical position of the sensor assembly relative to the X-ray source.

Additionally, compressible metal washer 708 may remain substantially entirely between first surface 704 and second surface 706 during compression between the first surface 704 and the second surface 706, and is not extruded past the edges of first surface 704 and second surface 706. In this way, a precise and reproducible distance between first surface 704 and second surface 706 is maintained by alignment protrusion 710 while compressible metal washer 708 adjusts to the desired height and decreases thermal resistance across heat transfer bolted joint 700.

Figure 8:
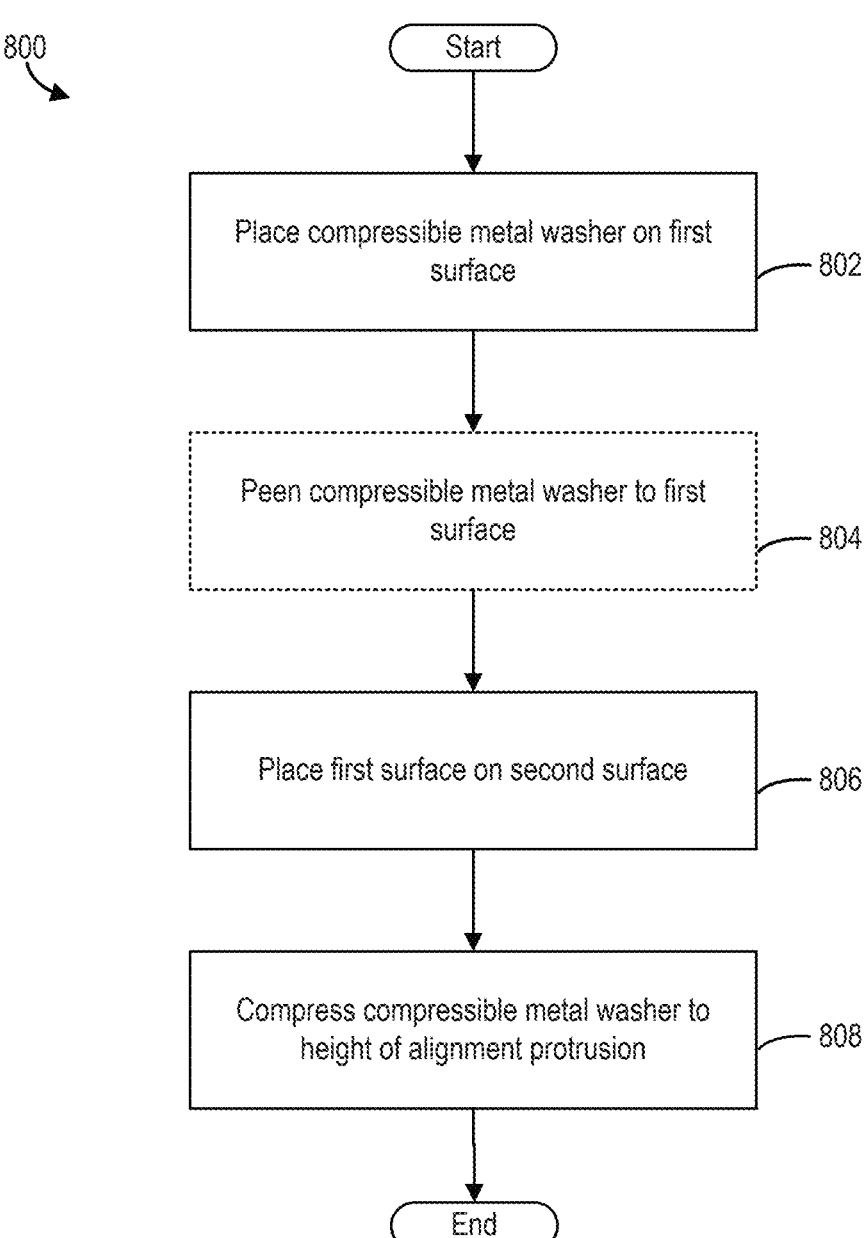
FIG. 8 shows a flowchart of an example of a method for assembling a heat transfer bolted joint, in accordance with one or more embodiments of the present disclosure.

Turning now to FIG. 8, a flowchart of a method 800 for forming a heat transfer bolted joint, such as heat transfer bolted joint 700 shown in FIG. 7 is shown. The heat transfer bolted joint may be formed between a first surface and a second surface. The first surface may be surface at an end of a beam assembly, such as beam assembly 310 and the second surface may be a surface of a rail assembly such as first rail assembly 318 and/or second rail assembly 320.

At 802, method 800 includes placing a compressible metal washer on the first surface. The compressible metal washer may be compressible metal washer 602 as shown in FIG. 6 and/or compressible metal washer 708 of FIG. 7. Placing the compressible metal washer on the first surface may include placing the compressible metal washer in face-sharing contact with the first surface and circumferentially surrounding an alignment protrusion of the first surface. An example of the compressible metal washer placed on the first surface is shown in FIG. 6.

At 804, method 800 optionally includes peening the compressible metal washer to the first surface. Peening may hold the compressible metal washer in place during assembly of the heat transfer bolted joint. Peening the compressible metal washer may be performed when the first surface includes divots for receiving the peening points of the compressible metal washer. Peening may include deforming the compressible metal washer into the divots to hold the compressible metal washer relative to the For example, peening the compressible metal washer may be demanded if the first surface is inverted with respect to a direction of gravity during assembly of the heat transfer bolted joint.

At 806, method 800 includes placing the first surface on the second surface. Placing the first surface on the second surface may include placing the alignment protrusion of the first surface in face-sharing contact with the second surface and placing the compressible metal washer in face-sharing contact with the second surface. In this way, the compressible metal washer may be sandwiched between the first surface and the second surface as shown in FIG. 7.

At 808, method 800 includes compressing compressible metal washer to a height of alignment protrusion. Compressing the compressible metal washer may include bolting the first surface to the second surface. The bolts may extend through the first surface and the second surface and may apply pressure between the first surface and the second surface. Bolting the first surface to the second surface may compress the compressible metal washer to a height equivalent to the height of the alignment protrusion. In this way, the pressure applied by the bolts may be a pressure sufficient to compress the compressible metal washer to the height equivalent to the height of the alignment protrusion and place the alignment protrusion in face-sharing contact with the second surface. Method 800 ends.

Turning now to FIG. 9, a graph 900 is shown of thermal resistance as a function of pressure applied to a heat transfer bolted joint, such as heat transfer bolted joint 700 of FIG. 7. The amount of compression experienced by the compressible metal washer as a function of pressure may be function of relative heights of the pristine compressible metal washer and height of the alignment protrusion. For example, a high contact pressure may be achieved by a large difference in height between the pristine compressible metal washer and the height of the alignment protrusion and contact pressure may be lowered by a decreasing the height difference between the pristine compressible metal washer and the height of the alignment protrusion.

Data points 902 of graph 900 correspond to measured relative thermal resistance measured at different contact pressures. Thermal resistance decreases as contact pressure increase up to a threshold contact pressure indicated by line 904. Past the threshold contact pressure, relative thermal resistance does not significantly (e.g., varies by more than 5%) as contact pressure increases. As shown in graph 900, the lowest thermal resistance may be reached at higher contact pressures, which may be achieved by the small height difference as described above or without the alignment protrusion at all. However, the alignment protrusion may be demanded for a precise and consistent height of the compressible metal washer in the heat transfer bolted joint. Additionally, without the alignment protrusion the compression may cause the compressible metal washer to extrude from between the first surface and second surface, thereby degrading heat transfer performance over time.

Turning now to FIG. 10, a heat map 1000 representative of contact pressure of the heat transfer bolted joint (such as heat transfer bolted joint 700 of FIG. 7) calculated by finite element modeling is shown. A first area 1002 corresponds to a region of highest pressure of the heat transfer bolted joint and equivalent to about $2\times10^7$ Pa. The first area 1002 may correspond to the area of the alignment protrusion most proximal to the bolt holes 1003, where there is direct contact between the first surface and the second surface. A second area 1004 corresponds to second high pressure region, where the pressure at the second area 1004 is lower than a pressure of the first area 1002 and is in a range of $1.75\times10^7$ Pa to $1\times10^7$ Pa. A third area 1006 corresponds to a lower pressure region where the pressure at the third area 1006 is lower than that of second area 1004 and in range of $0.75\times10^6$ Pa to $2.5\times10^6$. A fourth area 1008 corresponds to a lowest pressure region, where there is no contact pressure. As shown in heat map 1000, the alignment protrusion benefits from circumferentially surrounding bolt holes 1003 to have the highest contact pressure. For this reason, a thermal conductivity between the first surface in direct face-sharing contact with the second surface may be sufficient. As the areas move away from bolt holes 1003, pressure decreases and these areas may correspond to areas where the compressible metal washer is present. In this way the compressible metal washer may help to increase thermal conductivity between the first surface and the second surface in areas where the contact pressure is not as high or nonexistent.

The technical effect of the heat transfer bolted joint is to join the first surface to the second surface in such a way that heat transfer between the first surface and second surface is increased and the first surface is positioned precisely and accurately in three dimensions (e.g., laterally, longitudinally, and vertically) with respect to the second surface.

The disclosure also provides support for a heat transfer bolted joint of an X-ray detector module, comprising: a first surface comprising an alignment protrusion, a first alignment datum vertically extending from the alignment protrusion, a first bolt hole passing through the alignment protrusion, a compressible metal washer circumferentially surrounding the alignment protrusion and in direct face-sharing contact with the first surface, wherein the compressible metal washer is compressible in a vertical direction and is positioned essentially within the heat transfer bolted joint, and a second surface including a second alignment datum adapted to mate to the first alignment datum, and a second bolt hole passing through the second surface, wherein the second surface is in direct face-sharing contact with the compressible metal washer and the alignment protrusion. In a first example of the system, a vertical height of the alignment protrusion is equivalent to a vertical height of the compressible metal washer. In a second example of the system, optionally including the first example, the compressible metal washer is compressed to the vertical height of the alignment protrusion. In a third example of the system, optionally including one or both of the first and second examples, the compressible metal washer is formed of indium or an alloy of indium. In a fourth example of the system, optionally including one or more or each of the first through third examples, the compressible metal washer is solid at an operating temperature of the X-ray detector module. In a fifth example of the system, optionally including one or more or each of the first through fourth examples, a thermal conductivity of the compressible metal washer is at least 80 W/mK. In a sixth example of the system, optionally including one or more or each of the first through fifth examples, the compressible metal washer is affixed to the first surface by peening points.

The disclosure also provides support for a detector module of a computed tomography imaging system, comprising: a first rail assembly and second rail assembly positioned parallel to each other along lateral sides of the detector module, a beam assembly comprised of a heat transfer portion extending between the first rail assembly and second rail assembly, wherein a first end of the beam assembly is physically coupled to the first rail assembly by a first heat transfer bolted joint and a second end, laterally opposite the first end of the beam assembly is physically coupled to the second rail assembly by a second heat transfer bolted joint, wherein the first heat transfer bolted joint and second heat transfer bolted joint each include a compressible metal washer circumferentially surrounding an alignment protrusion protruding from a surface at the first and second ends of the beam assembly, respectively, and wherein a surface of the first and second rail assemblies included in the first and second heat transfer bolted joints respectively, is in face-sharing contact with the alignment protrusion and the compressible metal washer. In a first example of the system, a lateral length of the first heat transfer bolted joint is equivalent to a lateral length of the first rail assembly and a lateral length of the second heat transfer bolted joint is equivalent to a lateral length of the second rail assembly. In a second example of the system, optionally including the first example, the beam assembly includes a bracket portion extending vertically from the heat transfer portion and positioned between inner sides of the first rail assembly and second rail assembly. In a third example of the system, optionally including one or both of the first and second examples, heat is transferred from the beam assembly to the first rail assembly and the second rail assembly. In a fourth example of the system, optionally including one or more or each of the first through third examples, the first and second ends of the beam assembly each include a beam alignment datum and a pair of bolt holes passing through the alignment protrusion. In a fifth example of the system, optionally including one or more or each of the first through fourth examples, the beam alignment datum is positioned longitudinally between the pair of bolt holes. In a sixth example of the system, optionally including one or more or each of the first through fifth examples, a longitudinal and lateral position of the beam assembly relative to the first and second rail assemblies is controlled by the beam alignment datum mated to a rail alignment datum, the rail alignment datum positioned on a vertical surface of each of the first and second rail assemblies.

The disclosure also provides support for a computed tomography system, comprising: an X-ray source, configured to project a beam of X-ray radiation for use in imaging a subject, a detector module, configured to receive X-rays that pass through the subject to acquire projection data, the detector module comprising: a plurality of photon counting computed tomography (PCCT) detector units, each of the plurality of PCCT detector units stacked in a longitudinal direction within the detector module and each of the plurality of PCCT detector units including a sensor assembly physically coupled to a beam assembly, wherein the sensor assembly is configured to interact with the received X-rays, a first rail assembly physically coupled to a first end of the beam assembly of each of the plurality of PCCT detector units, and a second rail assembly positioned parallel to the first rail assembly and physically coupled a second end of the beam assembly of each of the plurality of PCCT detector units, wherein each interface between the first end of each beam assembly and the first rail assembly and between the second end of each beam assembly and the second rail assembly are formed as a heat transfer bolted joint, the heat transfer bolted joint including a compressible metal washer circumferentially surrounding an alignment protrusion protruding from a first surface of the heat transfer bolted joint, wherein a vertical height of the heat transfer bolted joint is determined by a vertical height of the alignment protrusion. In a first example of the system, the sensor assembly generates heat that is transferred to the first and second rail assemblies through the heat transfer bolted joints. In a second example of the system, optionally including the first example, a clearance between adjacent PCCT detector units of the plurality of PCCT detector units is in a range of 0.025 mm to 0.035 mm. In a third example of the system, optionally including one or both of the first and second examples, an alignment datum protrudes from the alignment protrusion, wherein the alignment datum controls a longitudinal and lateral position of the beam assembly with respect to the first and second rail assemblies. In a fourth example of the system, optionally including one or more or each of the first through third examples, the vertical height of the heat transfer bolted joint is calibrated to a demanded vertical position of the sensor assembly relative to the X-ray source. In a fifth example of the system, optionally including one or more or each of the first through fourth examples, a pressure in the heat transfer bolted joint is highest at an interface of the alignment protrusion and a second surface of the heat transfer bolted joint.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

FIGS. 1 and 3-7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A heat transfer bolted joint of an X-ray detector module, comprising:
   a first surface comprising an alignment protrusion;
   a first alignment datum vertically extending from the alignment protrusion;
   a first bolt hole passing through the alignment protrusion;
   a compressible metal washer circumferentially surrounding the alignment protrusion and in direct face-sharing contact with the first surface, wherein the compressible metal washer is compressible in a vertical direction and is positioned essentially within the heat transfer bolted joint; and
   a second surface including a second alignment datum adapted to mate to the first alignment datum, and a second bolt hole passing through the second surface, wherein the second surface is in direct face-sharing contact with the compressible metal washer and the alignment protrusion.

2. The heat transfer bolted joint of claim 1, wherein a vertical height of the alignment protrusion is equivalent to a vertical height of the compressible metal washer.

3. The heat transfer bolted joint of claim 2, wherein the compressible metal washer is compressed to the vertical height of the alignment protrusion.

4. The heat transfer bolted joint of claim 1, wherein the compressible metal washer is formed of indium or an alloy of indium.

5. The heat transfer bolted joint of claim 1, wherein the compressible metal washer is solid at an operating temperature of the X-ray detector module.

6. The heat transfer bolted joint of claim 1, wherein a thermal conductivity of the compressible metal washer is at least 80 W/mK.

7. The heat transfer bolted joint of claim 1, wherein the compressible metal washer is affixed to the first surface by peening points.

8. A detector module of a computed tomography imaging system, comprising:
   a first rail assembly and second rail assembly positioned parallel to each other along lateral sides of the detector module;

a beam assembly comprised of a heat transfer portion extending between the first rail assembly and second rail assembly,
   wherein a first end of the beam assembly is physically coupled to the first rail assembly by a first heat transfer bolted joint and a second end, laterally opposite the first end of the beam assembly is physically coupled to the second rail assembly by a second heat transfer bolted joint,
   wherein the first heat transfer bolted joint and second heat transfer bolted joint each include a compressible metal washer circumferentially surrounding an alignment protrusion protruding from a surface at the first and second ends of the beam assembly, respectively;
   wherein a first alignment datum vertically extends from the alignment protrusion; and
   wherein a surface of the first and second rail assemblies included in the first and second heat transfer bolted joints respectively, is in face-sharing contact with the alignment protrusion and the compressible metal washer.

9. The detector module of claim 8, wherein a lateral length of the first heat transfer bolted joint is equivalent to a lateral length of the first rail assembly and a lateral length of the second heat transfer bolted joint is equivalent to a lateral length of the second rail assembly.

10. The detector module of claim 8, wherein the beam assembly includes a bracket portion extending vertically from the heat transfer portion and positioned between inner sides of the first rail assembly and second rail assembly.

11. The detector module of claim 8, wherein heat is transferred from the beam assembly to the first rail assembly and the second rail assembly.

12. The detector module of claim 8, wherein the first and second ends of the beam assembly each include a beam alignment datum and a pair of bolt holes passing through the alignment protrusion.

13. The detector module of claim 12, wherein the beam alignment datum is positioned longitudinally between the pair of bolt holes.

14. The detector module of claim 12, wherein a longitudinal and lateral position of the beam assembly relative to the first and second rail assemblies is controlled by the beam alignment datum mated to a rail alignment datum, the rail alignment datum positioned on a vertical surface of each of the first and second rail assemblies.

15. A computed tomography system, comprising:
   an X-ray source, configured to project a beam of X-ray radiation for use in imaging a subject;
   a detector module, configured to receive X-rays that pass through the subject to acquire projection data, the detector module comprising:
      A plurality of photon counting computed tomography (PCCT) detector units, each of the plurality of PCCT detector units stacked in a longitudinal direction within the detector module and each of the plurality of PCCT detector units including a sensor assembly physically coupled to a beam assembly, wherein the sensor assembly is configured to interact with the received X-rays;
      a first rail assembly physically coupled to a first end of the beam assembly of each of the plurality of PCCT detector units; and a second rail assembly positioned parallel to the first rail assembly and physically coupled a second end of the beam assembly of each of the plurality of PCCT detector units, wherein each interface between the first end of each beam assembly and the first rail assembly and between the second end of each beam assembly and the second rail assembly are formed as a heat transfer bolted joint, the heat transfer bolted joint including a compressible metal washer circumferentially surrounding an alignment protrusion protruding from a first surface of the heat transfer bolted joint, wherein a first alignment datum vertically extends from the alignment protrusion; and wherein a vertical height of the heat transfer bolted joint is determined by a vertical height of the alignment protrusion.

16. The computed tomography system of claim 15, wherein the sensor assembly generates heat that is transferred to the first and second rail assemblies through the heat transfer bolted joints.

17. The computed tomography system of claim 15, wherein a clearance between adjacent PCCT detector units of the plurality of PCCT detector units is in a range of 0.025 mm to 0.035 mm.

18. The computed tomography system of claim 15, wherein the alignment datum controls a longitudinal and lateral position of the beam assembly with respect to the first and second rail assemblies.

19. The computed tomography system of claim 15, wherein the vertical height of the heat transfer bolted joint is calibrated to a demanded vertical position of the sensor assembly relative to the X-ray source.

20. The computed tomography system of claim 15, wherein a pressure in the heat transfer bolted joint is highest at an interface of the alignment protrusion and a second surface of the heat transfer bolted joint.

* * * * *